(12) United States Patent
Grinnell et al.

(10) Patent No.: US 6,268,337 B1
(45) Date of Patent: *Jul. 31, 2001

(54) METHODS FOR TREATING VASCULAR DISORDERS USING ACTIVATED PROTEIN C

(75) Inventors: Brian W. Grinnell; Daniel C Howey; Charles V Jackson, all of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/465,076

(22) Filed: Dec. 16, 1999

Related U.S. Application Data

(63) Continuation of application No. 09/161,900, filed on Sep. 28, 1998, now Pat. No. 6,037,322.
(60) Provisional application No. 60/064,765, filed on Nov. 7, 1997, now abandoned, provisional application No. 60/062,549, filed on Oct. 20, 1997, now abandoned, and provisional application No. 60/042,533, filed on Mar. 24, 1997, now abandoned.

(51) Int. Cl.[7] .................................................. A61K 38/36
(52) U.S. Cl. .................................. 514/8; 514/2; 514/12; 514/21; 435/69.6; 424/94.63; 424/94.64
(58) Field of Search .................................... 514/2, 12, 21, 514/8; 424/94.64, 94.63; 435/69.6

(56) References Cited

U.S. PATENT DOCUMENTS 5,084,274   1/1992   Griffin et al. ..................... 424/94.64
5,254,532  10/1993   Schwarz et al. ......................... 514/2
5,516,650   5/1996   Foster et al. ....................... 435/68.1
6,037,322 *  3/2000   Grinnell ................................ 514/8

OTHER PUBLICATIONS

Chabbat et al., Thromb. Haemost. 65: A1814, 1991 "The Behavriour of Human Activated Protein C in the Plasma of Different Laboratory Animals".
Frederick J. Walker, Thromb. Res. 22; 321–327, 1981, "Regulation of Bovine Activated Protein C by Protein S: The Role of the Cofactor Protein in Species Specificity".
Xuhua He, Bjorn Dahlback, Thromb. Haemost 71: 446–451, 1994, "Rabbit Plasma, unlike Its Human Counterpart, Contains no Complex between Protein S and C4b–Binding Protein".
Ralph E. Weinstein and Frederick J. Walker, Thromb. Res. 63: 123–131, 1991 "Species Specificity of the Fibrinoloytic Effects of Activated Protein C".
Andras Gruber and John H. Griffin, Blood 79:2340–2328, 1992, "Direct Detection of Activated Protein C in Blood From Human Subjects".

* cited by examiner

*Primary Examiner*—J. J. Moezie
(74) *Attorney, Agent, or Firm*—Brian P. Barrett; Steven P. Caltrider

(57) ABSTRACT

A method of treatment for patients with vascular occlusion and thromboembolic disorders including the acquired disease state of thrombotic stroke, by administering activated protein C. The administration of aPC provides a highly selective therapeutic agent with a low potential for causing bleeding complications. The administration of aPC is beneficial in preventing the local extension of the microvascular and macrovascular occluding arterial thrombus, thereby reducing the neurological deficit resulting from the stroke.

9 Claims, No Drawings

METHODS FOR TREATING VASCULAR DISORDERS USING ACTIVATED PROTEIN C

This application is a Continuation of U.S. Application Ser. No. 09/161,900, filed Sep. 28, 1998, now U.S. Pat. No. 6,037,322 which claims the benefit of PCT Application No. U.S. 98/05732, filed Mar. 24, 1998, U.S. Provisional Application Nos. 60/042,533 filed Mar. 24, 1997, now abandoned; 60/062,549 filed Oct. 20, 1997; and 60/064,765 filed Nov. 7, 1997 both are now abandoned.

FIELD OF THE INVENTION

This invention relates to medical science particularly the treatment of vascular disorders with activated protein C.

BACKGROUND OF THE INVENTION

Protein C is a serine protease and naturally occurring anticoagulant that plays a role in the regulation of homeostasis by deactivating Factors $V_a$ and $VIII_a$ in the coagulation cascade. Human protein C is made in vivo primarily in the liver as a single polypeptide of 461 amino acids. This precursor molecule undergoes multiple post-translational modifications including 1) cleavage of a 42 amino acid signal sequence; 2) proteolytic removal from the one chain zymogen of the lysine residue at position 155 and the arginine residue at position 156 to make the 2-chain form of the molecule, (i.e., a light chain of 155 amino acid residues attached through a disulfide bridge to the serine protease-containing heavy chain of 262 amino acid residues); 3) vitamin K-dependent carboxylation of nine glutamic acid residues clustered in the first 42 amino acids of the light chain, resulting in 9 gamma-carboxyglutamic acid residues; and 4) carbohydrate attachment at four sites (one in the light chain and three in the heavy chain). The heavy chain contains the well established serine protease triad of Asp 257, His 211 and Ser 360. Finally, the circulating 2-chain zymogen is activated in vivo by thrombin at a phospholipid surface in the presence of calcium ion. Activation results from removal of a dodecapeptide at the N-terminus of the heavy chain, producing activated protein C (aPC) possessing enzymatic activity.

In conjunction with other proteins, protein C functions as perhaps the most important down-regulator of blood coagulation. In other words the protein C enzyme system represents a major physiological mechanism of anticoagulation.

The coagulation system is best viewed as a chain reaction involving the sequential activation of zymogens into active serine proteases eventually producing the enzyme, thrombin, which through limited proteolysis converts plasma fibrinogen into the insoluble gel, fibrin. Two key events in the coagulation cascade are the conversion of clotting factor X to Xa by clotting factor IXa and the conversion of prothrombin into thrombin by clotting factor Xa. Both of these reactions occur on cell surfaces, most notably the platelet surface. Both of these reactions require cofactors. The major cofactors, factors V and VIII, in the system circulate as relatively inactive precursors, but when the first few molecules of thrombin are formed, thrombin loops back and activates the cofactors through limited proteolysis. The activated cofactors, Va and VIIIa, accelerate both the conversion of prothrombin into thrombin and also the conversion of factor X to factor Xa by approximately five orders of magnitude. Activated protein C overwhelmingly prefers two plasma protein substrates which it hydrolyzes and irreversibly destroys. These plasma protein substrates are the activated forms of the clotting cofactors, Va and VIIIa. Activated protein C only minimally degrades the inactive precursors, clotting factors V and VIII. Activated protein C in dogs has been shown to sharply increase circulating levels of the major physiological fibrinolytic enzyme, tissue plasminogen activator (tPA). Activated protein C has been shown in vitro to enhance the lysis of fibrin in human whole blood. Therefore, activated protein C represents an important adjunct to in vivo fibrinolysis in man.

Today, there are few effective treatments available for vascular occlusions, including thrombotic stroke. Treatment with tPA, if administered within three hours from the onset of the stroke, has been recently approved by the FDA. Treatment of strokes with either heparin or oral anticoagulants, although occasionally beneficial, carries a high risk for bleeding into the infarcted brain area.

The use of recombinant aPC (r-aPC) in the treatment of thrombotic occlusion or thromboembolism in a baboon model has been presented by Griffin, et al. in U.S. Pat. No. 5,084,274 and European Patent Specification EP 0 318 201 B1. Griffin claimed dose levels in the range of 0.07 mg/kg/hr to 1.1 mg/kg/hr for the treatment of thrombotic occlusion. However, applicants have found that these dose levels are in a range above the toxicological level of r-aPC. For example, pre-clinical toxicology studies in non-human primates indicate the safety of r-aPC for a 96 hour infusion is limited at a top dose of around 0.05 mg/kg/hr. Therefore, the lowest dose level taught by Griffin, et al., i.e. 0.07 mg/kg/hr, is at a level greater than the toxic dose established by applicants for humans. Thus, even the lowest dose level taught by Griffin would carry a high risk for bleeding into the infarcted brain area, thereby aggravating the neurological deficit accompanying the stroke. Accordingly, even in view of the teaching of Griffin, et al., there remains a need to identify an effective therapy of arterial thrombus formation in humans with aPC.

Contrary to the teachings of prior investigators, applicants have discovered that only low dose therapy with r-aPC is useful in the treatment of thrombotic stroke. The administration of aPC is also beneficial in preventing the local extension of the microvascular and macrovascular occluding arterial thrombus, thereby reducing the neurological deficit resulting from the stroke.

SUMMARY OF THE INVENTION

The present invention provides a method of treatment for human patients with vascular occlusive and arterial thromboembolic disorders, which comprises administering to said patient a dosage of about 0.01 mg/kg/hr to about 0.05 mg/kg/hr of activated protein C by continuous infusion for about 4 to about 96 hours.

This invention also provides an article of manufacture for human pharmaceutical use, comprising packaging material and a vial comprising lyophilized activated protein C, wherein said packaging material comprises a label which indicates that said activated protein C be administered at a dosage of about 0.01 mg/kg/hr to about 0.05 mg/kg/hr by continuous infusion for about 4 to about 96 hours.

DETAILED DESCRIPTION OF THE INVENTION

For purposes of the present invention, as disclosed and claimed herein, the following terms are as defined below.

Activated protein C (aPC) refers to recombinant activated protein C. aPC includes and is preferably human protein C although aPC may also include other species or derivatives having full protein C proteolytic, amidolytic, esterolytic, and biological (anticoagulant or pro-fibrinolytic) activities. Examples of protein C derivatives are described by Gerlitz, et al., U.S. Pat. No. 5,453,373, and Foster, et al., U.S. Pat. No. 5,516,650, the entire teachings of which are hereby included by reference. Recombinant activated protein C may be produced by activating recombinant human protein C zymogen in vitro or by direct secretion of the activated form of protein C. Protein C may be produced in procaryotic cells, eukaryotic cells, transgenic animals, transgenic plants, or gene therapy, including, for example, secretion from human kidney 293 cells as a zymogen then purified and activated by techniques known to the skilled artisan.

Continuous infusion—continuing substantially uninterrupted the introduction of a solution into a blood vessel for a specified period of time.

Bolus injection—the injection of a drug in a defined quantity (called a bolus) over a period of time up to about 120 minutes.

Suitable for administration—A formulation or solution preferably prepared from lyophilized aPC that is appropriate to be given as a therapeutic agent.

Zymogen—refers to secreted, inactive forms, whether one chain or two chains, of protein C.

The term "vial" refers broadly to a reservoir suitable for retaining the lyophilized activated protein C and diluent in a contained sterile state. Vials suitable for packaging products for parental administration are well-known and recognized in the art.

The present invention provides a method of treatment for human patients with vascular occlusive and arterial thromboembolic disorders which comprises administering to said patient a dosage of about 0.01 mg/kg/hr to about 0.05 mg/kg/hr of activated protein C by continuous infusion for about 4 to about 96 hours.

Applicants have found that pre-clinical toxicology studies in non-human primates indicate the safety of r-aPC for a 96 hour infusion is limited at a top dose of around 0.05 mg/kg/hr. These data are unexpected when compared to the prior art. In fact, the dose levels of r-aPC for humans that have been based on previous pre-clinical and clinical studies are above the toxicological range established in the above toxicological studies.

The present invention also demonstrates the effect of intravenous administration of r-aPC on reperfusion of totally occluded coronary arteries in a canine model of occlusive coronary artery thrombosis (Example 2). Surprisingly, five of six animals treated with r-aPC demonstrated vessel reperfusion compared to vessel reperfusion in none of the six control animals.

aPC administered in accordance with the present invention is useful in treating vascular occlusive or arterial thromboembolic disorders, including thrombotic stroke, peripheral arterial thrombosis, emboli originating from the heart or peripheral arteries, acute myocardial infarction, and coronary arterial disease without the concomitant bleeding problems that may be associated with high dose levels.

Furthermore, the present invention provides an article of manufacture comprising packaging material and a vial comprising a lyophilized formulation of activated protein C, wherein said packaging material comprises a label which indicates that said lyophilized formulation be stored at refrigerated temperature; that said lyophilized formulation be reconstituted with normal saline, sterile water or comparable diluent; that said reconstituted formulation may be stored at refrigerated temperature to about 22° C.; and that said reconstituted formulation be administered within 48 hours.

The present claimed articles of manufacture are useful for administration of aPC. Applicants have discovered that the reconstituted formulation of activated protein C may be administered at a dosage of about 0.01 mg/kg/hr to about 0.05 mg/kg/hr by continuous infusion for about 4 to about 96 hours.

The aPC can be formulated according to known methods to prepare pharmaceutically useful compositions. The aPC is preferably administered parenterally to ensure its delivery into the bloodstream in an effective form by injecting the appropriate dose as continuous infusion for about 4 to about 96 hours. Preferably, the appropriate dose of aPC will be administered by continuous infusion for about 4 to about 72 hours. More preferably, the appropriate dose of aPC will be administered by continuous infusion for about 4 to about 48 hours. More preferably, the appropriate dose of aPC will be administered by continuous infusion for about 12 to about 48 hours. More preferably, the appropriate dose of aPC will be administered by continuous infusion for about 12 to about 36 hours. More preferably, the appropriate dose of aPC will be administered by continuous infusion for about 4 to about 36 hours. More preferably, the appropriate dose of aPC will be administered by continuous infusion for about 12 to about 24 hours. Most preferably, the appropriate dose of aPC will be administered by continuous infusion for about 24 hours. The administration of aPC will begin as soon as possible following diagnosis of the vascular occlusive or arterial thromboembolic disorder.

The amount of aPC administered is from about 0.01 mg/kg/hr to about 0.05 mg/kg/hr which is equivalent to about 20 mg/70 kg/24 hours to about 84 mg/70 kg/24 hours. While the dose level is identified as a specific amount per 24 hours, one skilled in the art would recognize that this is a designation of the dose level and is not necessarily limited to a 24 hour infusion but may include continuous infusion for various times, for example, from about four hours to about ninety-six hours. More preferably the amount of aPC administered is about 0.01 mg/kg/hr to about 0.04 mg/kg/hr (about 20 mg/70 kg/24 hours to about 67 mg/70 kg/24 hours). While more preferably the amount of aPC administered will be about 0.01 mg/kg/hr to about 0.03 mg/kg/hr (about 20 mg/70 kg/24 hours to about 50 mg/70 kg/24 hours). Furthermore, the amount of aPC administered is from about 0.02 mg/kg/hr to about 0.05 mg/kg/hr which is equivalent to about 34 mg/70 kg/24 hours to about 84 mg/70 kg/24 hours. More preferably the amount of aPC administered is about 0.024 mg/kg/hr to about 0.048 mg/kg/hr (about 40 mg/70 kg/24 hours to about 80 mg/70 kg/24 hours). While more preferably the amount of aPC administered will be about 0.027 mg/kg/hr to about 0.045 mg/kg/hr (about 45 mg/70 kg/24 hours to about 75 mg/70 kg/24 hours). While more preferably the amount of aPC administered will be about 0.030 mg/kg/hr to about 0.042 mg/kg/hr (about 50 mg/70 kg/24 hours to about 70 mg/70 kg/24 hours). While more preferably the amount of aPC administered will be about 0.033 mg/kg/hr to about 0.039 mg/kg/hr (about 55 mg/70 kg/24 hours to about 65 mg/70 kg/24 hours). Preferable amounts of aPC administered are about 0.024 mg/kg/hr (about 40 mg/70 kg/24 hours), about 0.027 mg/kg/hr (about 45 mg/70 kg/24 hours) or, about 0.030 mg/kg/hr to about 0.042 mg/kg/hr (about 50 mg/70 kg/24 hours).

Alternatively, the aPC will be administered by injecting a portion of the appropriate dose per hour as a bolus injection over a time from about 5 minutes to about 120 minutes, followed by continuous infusion of the appropriate dose for about twenty three hours to about 96 hours which results in the appropriate dose administered over 24 hours to 96 hours.

As noted previously, the dosage levels of aPC presented above are in contrast to those presented by Griffin, et al. Griffin claimed dose levels in the range of 0.07 mg/kg/hr to 1.1 mg/kg/hr for the treatment of thrombotic occlusion. In contrast, the dose levels claimed herein are equivalent to a tenth of this dose or a range of about 0.01 mg/kg/hr to about 0.05 mg/kg/hr. The most preferable dose level of aPC to be administered for thrombolitic occlusion as described herein will be about 0.024 mg/kg/hr. It is significant to note that the most preferable dose level of 0.024 mg/kg/hr as indicated herein is 3 fold less than the lowest dose level claimed by Griffin and 44 fold less than the highest dose level claimed by Griffin.

Preparation 1

Preparation of Human Protein C

Recombinant human protein C (rHPC) was produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang, et al., U.S. Pat. No. 4,775,624, the entire teaching of which is incorporated herein by reference. The plasmid used to express human protein C in 293 cells was plasmid pLPC which is disclosed in Bang, et al., U.S. Pat. No. 4,992,373, the entire teaching of which is incorporated herein by reference. The construction of plasmid pLPC is also described in European Patent Publication No. 0 445 939, and in Grinnell, et al., 1987, *Bio/Technology* 5:1189–1192, the teachings of which are also incorporated herein by reference. Briefly, the plasmid was transfected into 293 cells, then stable transformants were identified, subcultured and grown in serum-free media. After fermentation, cell-free medium was obtained by microfiltration.

The human protein C was separated from the culture fluid by an adaptation of the techniques of Yan, U.S. Pat. No. 4,981,952, the entire teaching of which is herein incorporated by reference. The clarified medium was made 4 mM in EDTA before it was absorbed to an anion exchange resin (Fast-Flow Q, Pharmacia). After washing with 4 column volumes of 20 mM Tris, 200 mM NaCl, pH 7.4 and 2 column volumes of 20 mM Tris, 150 mM NaCl, pH 7.4, the bound recombinant human protein C zymogen was eluted with 20 mM Tris, 150 mM NaCl, 10 mM $CaCl_2$, pH 7.4. The eluted protein was greater than 95% pure after elution as judged by SDS-polyacrylamide gel electrophoresis.

Further purification of the protein was accomplished by making the protein 3 M in NaCl followed by adsorption to a hydrophobic interaction resin (Toyopearl Phenyl 650M, TosoHaas) equilibrated in 20 mM Tris, 3 M NaCl, 10 mM $CaCl_2$, pH 7.4. After washing with 2 column volumes of equilibration buffer without $CaCl_2$, the recombinant human protein C was eluted with 20 mM Tris, pH 7.4.

The eluted protein was prepared for activation by removal of residual calcium. The recombinant human protein C was passed over a metal affinity column (Chelex-100, Bio-Rad) to remove calcium and again bound to an anion exchanger (Fast Flow Q, Pharmacia). Both of these columns were arranged in series and equilibrated in 20 mM Tris, 150 mM NaCl, 5 mM EDTA, pH 6.5. Following loading of the protein, the Chelex-100 column was washed with one column volume of the same buffer before disconnecting it from the series. The anion exchange column was washed with 3 column volumes of equilibration buffer before eluting the protein with 0.4 M NaCl, 20 mM Tris-acetate, pH 6.5. Protein concentrations of recombinant human protein C and recombinant activated protein C solutions were measured by UV 280 nm extinction $E^{0.1\%}$=1.85 or 1.95, respectively.

Preparation 2

Activation of Recombinant Human Protein C

Bovine thrombin was coupled to Activated CH-Sepharose 4B (Pharmacia) in the presence of 50 mM HEPES, pH 7.5 at 4° C. The coupling reaction was done on resin already packed into a column using approximately 5000 units thrombin/ml resin. The thrombin solution was circulated through the column for approximately 3 hours before adding MEA to a concentration of 0.6 ml/l of circulating solution. The MEA-containing solution was circulated for an additional 10–12 hours to assure complete blockage of the unreacted amines on the resin. Following blocking, the thrombin-coupled resin was washed with 10 column volumes of 1 M NaCl, 20 mM Tris, pH 6.5 to remove all non-specifically bound protein, and was used in activation reactions after equilibrating in activation buffer.

Purified rHPC was made 5 mM in EDTA (to chelate any residual calcium) and diluted to a concentration of 2 mg/ml with 20 mM Tris, pH 7.4 or 20 mM Tris-acetate, pH 6.5. This material was passed through a thrombin column equilibrated at 37° C. with 50 mM NaCl and either 20 mM Tris pH 7.4 or 20 mM Tris-acetate pH 6.5. The flow rate was adjusted to allow for approximately 20 min. of contact time between the rHPC and thrombin resin. The effluent was collected and immediately assayed for amidolytic activity. If the material did not have a specific activity (amidolytic) comparable to an established standard of aPC, it was recycled over the thrombin column to activate the rHPC to completion. This was followed by 1:1 dilution of the material with 20 mM buffer as above, with a pH of anywhere between 7.4 or 6.0 (lower pH being preferable to prevent autodegradation) to keep the aPC at lower concentrations while it awaited the next processing step.

Removal of leached thrombin from the aPC material was accomplished by binding the aPC to an anion exchange resin (Fast Flow Q, Pharmacia) equilibrated in activation buffer (either 20 mM Tris, pH 7.4 or preferably 20 mM Tris-acetate, pH 6.5) with 150 mM NaCl. Thrombin passes through the column and elutes during a 2–6 column volume wash with 20 mM equilibration buffer. Bound aPC is eluted with a step gradient using 0.4 M NaCl in either 5 mM Tris-acetate, pH 6.5 or 20 mM Tris, pH 7.4. Higher volume washes of the column facilitated more complete removal of the dodecapeptide. The material eluted from this column was stored either in a frozen solution (−20° C.) or as a lyophilized powder.

The amidolytic activity (AU) of aPC was determined by release of p-nitroanaline from the synthetic substrate H-D-Phe-Pip-Arg-p-nitroanilide (S-2238) purchased from Kabi Vitrum using a Beckman DU-7400 diode array spectrophotometer. One unit of activated protein C was defined as the amount of enzyme required for the release of 1 μmol of p-nitroaniline in 1 min. at 25° C., pH 7.4, using an extinction coefficient for p-nitroaniline at 405 nm of 9620 $M^{-1}cm^{-1}$.

The anticoagulant activity of activated protein C was determined by measuring the prolongation of the clotting time in the activated partial thromboplastin time (APTT)

clotting assay. A standard curve was prepared in dilution buffer (1 mg/ml radioimmunoassay grade BSA, 20 mM Tris, pH 7.4, 150 mM NaCl, 0.02% $NaN_3$) ranging in protein C concentration from 125–1000 ng/ml, while samples were prepared at several dilutions in this concentration range. To each sample cuvette, 50 μl of cold horse plasma and 50 μl of reconstituted activated partial thromboplastin time reagent (APTT Reagent, Sigma) were added and incubated at 37° C. for 5 min. After incubation, 50 μl of the appropriate samples or standards were added to each cuvette. Dilution buffer was used in place of sample or standard to determine basal clotting time. The timer of the fibrometer (CoA Screener Hemostasis Analyzer, American Labor) was started upon the addition of 50 μl 37° C. 30 mM $CaCl_2$ to each sample or standard. Activated protein C concentration in samples are calculated from the linear regression equation of the standard curve. Clotting times reported here are the average of a minimum of three replicates, including standard curve samples.

The above descriptions enable one with appropriate skill in the art to prepare aPC for utilization it in the treatment of thrombotic stroke.

EXAMPLE 1

Human Plasma Levels of aPC

Six human patients received an i.v. infusion of aPC at 1 mg/m² /hour or about 0.024 mg/kg/hr over a 24 hour period. The aPC administered was a lyophilized formulation containing 10 mg aPC, 5 mM Tris acetate buffer and 100 mM sodium chloride reconstituted with two ml of water and adjusted to pH 6.5.

Plasma concentrations of aPC were measured using an Immunocapture-Amidolytic Assay. Blood was collected in the presence of citrate anticoagulant and benzamidine, a reversible inhibitor of aPC. The enzyme was captured from plasma by an aPC specific murine monoclonal antibody, C3, immobilized on a microtiter plate. The inhibitor was removed by washing and the amidolytic activity or aPC was measured using an oligopeptide chromogenic substrate. Following incubation for 16–20 h at 37° C., the absorbance was measured at 405 nm and data are analyzed by a weighted linear curve-fitting algorithm. aPC concentrations were estimated from a standard curve ranging in concentrations from 0–100 ng/ml. The limit of quantitation of the assay was 1.0 ng/ml. The aPC dose levels and plasma concentrations were measured at about 24 hours. The plasma ranges are from 2 ng/ml to less than 100 ng/ml. The preferred plasma ranges are from about 20 ng/ml to 80 ng/ml. Most preferably plasma ranges are from about 30 ng/ml to about 60 ng/ml and still more preferably about 50 ng/ml. Thus, the dose of 0.024 mg/kg/hr yields the most preferable plasma concentration of 50 ng/ml at 24 hours for treatment of thrombotic stroke without the concomitant bleeding problems from higher dose levels.

EXAMPLE 2

Induced Reperfusion in a Canine Model of Occlusive Coronary Artery Thrombosis Twelve dogs (17–22 kg, either sex, Butler Farms) were anesthetized with sodium pentobarbital (30 mg/kg, i.v.) and ventilated with room air. Cannulas were placed for measurement of blood pressure, drug administration and blood sampling in the carotid artery, femoral vein, and jugular vein; respectively. A left thoracotomy was performed, the heart was suspended in a pericardial cradle and a 2 cm segment of the left circumflex coronary artery (LCCA) was isolated proximal to the first main diagonal branch. The LCCA was instrumented with an electromagnetic flow probe, stimulating electrode, and an external occluder to measure coronary blood flow, produce vessel injury, and provide critical stenosis; respectively. Vessel injury was caused by placing the stimulating electrode (anode) in contact with the intimal side of the vessel and stimulating the anode with 100 μA d.c. current (the circuit was completed by placing the cathode in a subcutaneous site). The injury current was continued for 60 minutes and then stopped whether the vessel has occluded or not. Vessels reached total occlusion in approximately 60 minutes from the initiation of vessel injury. Thirty minutes after total vessel occlusion (established as zero coronary blood flow for 30 minutes) a continuous intravenous infusion of 2.0 mg/kg/hr aPC or 20 ml TRIS buffer, pH 7.4 (vehicle group) was infused for 2 hr. The preparations were followed for 4 hrs beginning from the point of initiation of LCCA injury. Arterial blood pressure, heart rate and coronary blood flow were acquired and analyzed. At different time points throughout the experiment, blood samples were drawn to determine whole blood clotting times (Hemochron 801), and gingival template bleeding times were determined using a Simplate II bleeding time device. A second set of blood samples (citrated) were collected throughout the experiment for determination of plasma plasminogen activator inhibitor-1 (PAI-1). Plasma PAI-1 levels were determined using an IMUBIND™ plasma PAI-1 ELISA kit (American Diagnostica). All data (reported as mean±SEM) were analyzed for statistical differences using single ANOVA followed by Student-Neuman-Keuls analysis for significance at the level p<0.05. Incidence of reperfusion and patency were analyzed using Fisher's Exact test at a level of p<0.05.

A continuous infusion of 2.0 mg/kg/hr aPC produced a 6 fold increase in APTT whole blood clotting time by the end of the 2 hr drug infusion (table 1). APTT had begun to return to normal values by the end of the experiment. There was no observable effect on thrombin clotting time or template bleeding time. Results are set forth in Table 2.

TABLE 2

Effects of aPC on Coagulation and Template Bleeding Times in the Anesthetized Dog

| Treatment | Parameter | Predrug | 60 min Inf. | 120 min Inf. | End |
|---|---|---|---|---|---|
| Vehicle[a] | Thrombin Time (sec) | 36 ± 1 | 38 ± 4 | 33 ± 1 | 34 ± 1 |
| (n = 6) | APTT (sec) | 100 ± 6 | 95 ± 5 | 89 ± 10 | 91 ± 10 |
| | Template Bleeding | 132 ± 15 | 182 ± 14 | 152 ± 15 | 159 ± 13 |

TABLE 2-continued

Effects of aPC on Coagulation and Template Bleeding Times in the Anesthetized Dog

| Treatment | Parameter | Predrug | 60 min Inf. | 120 min Inf. | End |
|---|---|---|---|---|---|
| aPC* (n = 6) | Thrombin Time (sec) | 33 ± 1 | 34 ± 1 | 34 ± 1 | 34 ± 1 |
| | APTT (sec) | 96 ± 6 | 573 ± 237 | 670 ± 209 * | 138 ± 13 * |
| | Template Bleeding Time (sec) | 199 ± 41 | 272 ± 84 | 204 ± 20 | 193 ± 39 |

The dosing regimen used for the Vehicle group was 20 ml of TRIS-Buffered Saline infused for 2 hr. and aPC (2.0 mg/kg/hr × 2 h) administration began 30 minutes after total vessel occlusion.
*Denotes a statistical difference at the level p<.05 versus the vehicle group. Each value represents the mean ± SEM.

Table 3 illustrates the effects of intravenous administration of aPC on reperfusion of totally occluded coronary arteries. Time to total thrombotic occlusion of the coronary arteries was similar between the 2 groups; 66±7 and 62±6 minutes, vehicle-treated and aPC-treated, respectively. Five of six vessels in the aPC-treated group demonstrated reperfusion compared to none of the 6 vessels receiving vehicle; time to reperfusion in the aPC-treated group was 128±17 min. Coronary blood flow in the aPC treated group was significantly greater than the corresponding vehicle-treated group; the aPC-treated group reached 13.7±2.7 ml/min during the reperfusion period and a flow volume of 1069±623 ml (this represents a restoration of approximately 60–70% of the pre-thrombosis coronary blood flow in this group). Three of the 5 vessels exposed to aPC were still patent at the end of the 4 hr experiment. Thus, the data demonstrates that aPC is effective in the treatment of occlusive coronary artery thrombosis in a canine model.

TABLE 3

Effects of aPC on Restoration of Coronary Blood Flow in the Canine Coronary Artery Thrombosis Model

| Parameter | Vehicle (n = 6) | aPC (n = 6) |
|---|---|---|
| Time to Occlusion (min) | 66 ± 7 | 62 ± 6 |
| Thrombus Mass (mg) | 10.8 ± 2.1 | 8.2 ± 1.2 |
| Incidence of Reperfusion | 0 | 5 of 6* |
| Time to Reperfusion (min) | 0 | 128 ± 17* |
| Vessel Patency @ End of Experiment | 0 of 6 | 3 of 5 |
| CBF during Reperfusion (ml/min) | 0 | 13.7 ± 2.7* |
| Reperfusion Volume (ml) | 0 | 1069 ± 623 |

*Denotes a statistical difference at the level p < .05 versus the vehicle group. Each value represents the mean ± SEM.

Blood samples drawn throughout the each experiment demonstrated that there was a significant correlation with the intravenous infusion of aPC and circulating levels of plasminogen activator inhibitor-1 (PAI-1). By the end of the intravenous infusion of aPC, plasma PAI-1 levels had decreased by 80%. Upon cessation of the infusion of aPC, plasma PAI-1 levels began to return to pre-infusion levels.

Although these dosage levels in this canine model appear to be higher than the claimed dosage levels for humans, Applicants have found that the dog is especially insensitive to human activated protein C, therefore the claimed dosage levels are appropriate for humans.

What is claimed is:

1. A method of treating human patients with vascular occlusive and arterial thromboembolic disorders, which comprises administering to said patient a dosage of about 0.01 mg/kg/hr to about 0.05 mg/kg/hr of activated protein C by continuous infusion for a time under conditions effective to ameliorate the vascular occlusive and arterial tromboembolic disorders.

2. The method of claim 1 wherein the vascular occlusive or thromboembolic disorder is thrombotic stroke.

3. The method according to claim 2 which comprises administering to said patient about 0.02 mg/kg/hr to about 0.03 mg/kg/hr activated protein C.

4. The method according to claim 3 wherein the activated protein C is human activated protein C.

5. The method according to claim 4 wherein the dosage is about 0.024 mg/kg/hr human activated protein C.

6. The method according to claim 4 which comprises administering about 0.027 mg/kg/hr activated protein C.

7. The method according to claim 4 which comprises administering about 0.030 mg/kg/hr activated protein C.

8. The method of claim 1 wherein the activated protein C is administered in a bolus injection followed by said continuous infusion for about 96 hours.

9. The method of claim 8 wherein the activated protein C is administered in a bolus injection in about 5 minutes to about 120 minutes.

* * * * *

UNITED STATES PATENT AND TRADEMARK OFFICE
CERTIFICATE OF CORRECTION

PATENT NO. : 6,268,337 B1
DATED : July 31, 2001
INVENTOR(S) : Brian W. Grinnell, Daniel C. Howey, Charles V. Jackson It is certified that error appears in the above-identified patent and that said Letters Patent is hereby corrected as shown below:

Claim 1,
Line 6, the last word, please correct the typographical error from "tromboembolic" to -- thromboembolic. --

Signed and Sealed this

Nineteenth Day of March, 2002

Attest:

JAMES E. ROGAN
Attesting Officer    Director of the United States Patent and Trademark Office